(12) United States Patent
Fabre et al.

(10) Patent No.: US 8,961,997 B2
(45) Date of Patent: Feb. 24, 2015

(54) METHOD FOR PURIFYING THE RABIES VIRUS

(75) Inventors: Virginie Fabre, Lyons (FR); Céline Rocca, Bibost (FR); Pierre Riffard, Dommartin (FR); Eric Calvosa, Haute Rivoire (FR)

(73) Assignee: Sanofi Pasteur SA, Lyons (FR)

( * ) Notice: Subject to any disclaimer, the term of this patent is extended or adjusted under 35 U.S.C. 154(b) by 706 days.

(21) Appl. No.: 12/756,590

(22) Filed: Apr. 8, 2010

(65) Prior Publication Data

US 2010/0260798 A1    Oct. 14, 2010

Related U.S. Application Data

(60) Provisional application No. 61/231,394, filed on Aug. 5, 2009.

(30) Foreign Application Priority Data

Apr. 8, 2009    (FR) ...................................... 09 52310

(51) Int. Cl.
*B01D 15/08* (2006.01)
*B01D 15/00* (2006.01)
*C02F 1/42* (2006.01)
*A61K 39/205* (2006.01)
*C12N 7/00* (2006.01)
*A61K 39/12* (2006.01)

(52) U.S. Cl.
CPC . *C12N 7/00* (2013.01); *A61K 39/12* (2013.01); *C12N 2760/20151* (2013.01)
USPC ......... 424/224.1; 424/204.1; 435/5; 210/656; 210/660; 210/661; 210/679; 210/685

(58) Field of Classification Search
None
See application file for complete search history.

(56) References Cited

U.S. PATENT DOCUMENTS

| 4,525,349 A | 6/1985 | Montagnon |
| 4,664,912 A | 5/1987 | Wiktor et al. |
| 4,725,547 A | 2/1988 | Sakamoto et al. |
| 6,008,036 A | 12/1999 | Fanget et al. |

FOREIGN PATENT DOCUMENTS

| EP | 0171771 A2 | 2/1986 |
| EP | 1724338 A1 | 11/2006 |
| WO | 97/06243 | 2/1997 |
| WO | 2004/112707 | 12/2004 |
| WO | 2008/071774 | 6/2008 |
| WO | 2009/109086 | 9/2009 |

OTHER PUBLICATIONS

Aaslestad and Wiktor. Recovery of Protective Activity in Rabies Virus Vaccines Concentrated and Purified by Four Different Methods. Appl Microbiol. 1972; 24(1): 37-43.*

Forrer, M. Antibody Purification With Ion-Exchange Chromatography. ETH Diss. No. 17784, 2008.*

Rourou, et al. A microcarrier cell culture process for propagating rabies virus in Vero cells grown in a stirred bioreactor under fully animal component free conditions. Vaccine. 2007; 25:3879-3889.*

Sun, et al. Urea-nuclease treatment of concentrated retrovirions preserves viral RNA and removes polymerase chain reaction-amplifiable cellular RNA and DNA. J. Virol. Met. 2006; 137(2): 304-308.*

Follmann, et al. Safety of Lyophilized SAG2 Oral Rabies Vaccine in Collared Lemmings. Journal of Wildlife Disease. 2002;, 38(1): 216-218.*

Dietzschold, et al. Isolation and Purification of a Polymeric Form of the Glycoprotein of Rabies Virus. J. gen. Virol. 1978; 40: 131-139.*

Jacob and Schluter Ion Exchange Chromatography for the Purification of Monoclonal Antibodies (MAbs). Bioprocessing & Biopartnering. 2006: 32-35.*

Sigma Data Sheet—Lysozyme downloaded Apr. 16, 2013.*

Agrisera Antibodies downloaded Apr. 16, 2013.*

Frazzati-Gallina et al. "Higher production of rabies virus in serum-free medium cell cultures on microcarriers"; Journal of Biotechnology 92 (2001) 67-72.

Rourou et al. "A microcarrier cell culture process for propagating rabies virus in Vero cells grown in a stirred bioreactor under fully animal component free conditions"; Vaccine 25 (2007) 3879-3889.

Frazzati-Gallina et al. "Vero-cell rabies vaccine produced using serum-free medium"; Vaccine 23 (2004) 511-517.

Ananda Arone Prem Kumar et al. "Process standardization for optimal virus recovery and removal of substrate DNA and bovine serum proteins in Vero cell-derived rabies vaccine"; Journal of Bioscience and Bioengineering; vol. 94, No. 5, 375-383 (2002).

Ananda Arone Prem Kumar et al. "Purification potency and immunogenecity analysis of Vero cell culture-derived rabies vaccine: a comparative study of single-step column chromatography and zonal centrifuge purification"; Microbes and Infection ; 7 (2005) 1110-1116.

Jallet et al. "Chimeric Lyssavirus glycoproteins with increased immunological potential"; Journal of Virology (Jan. 1999); vol. 73 No. 1—pp. 225-233.

(Continued)

*Primary Examiner* — Zachariah Lucas
*Assistant Examiner* — Stuart W Snyder
(74) *Attorney, Agent, or Firm* — McDonnell Boehnen Hulbert & Berghoff LLP

(57) ABSTRACT

The subject of the invention is a method for purifying the rabies virus, comprising a single ion-exchange chromatography step, said step being cation exchange chromatography according to which:

a) the supernatant of a culture of cells infected with this virus is brought into contact with a cation exchange chromatography support comprising a polymethacrylate matrix onto which sulfoisobutyl groups have been grafted such that the rabies virus binds to this support, and;

b) the virus is eluted from its support.

17 Claims, No Drawings

(56) References Cited

OTHER PUBLICATIONS

Jungbauer et al. "Polymethacrylate monoliths for preparative and industrial separation of biomolecular assemblies"; Journal of Chromatography A—1184 (2008) 62-79.

Search Report issued by French Patent Office for FR 0952310.

GE Healthcare, "Capto S cation exchanger for post-Protein A purification of monoclonal antibodies," Application Note 28-4078-17 AA, Ion exchange chromatography, 2006, pp. 1-6.

* cited by examiner

METHOD FOR PURIFYING THE RABIES VIRUS

CROSS-REFERENCE TO RELATED APPLICATIONS

This application claims the benefit of priority of U.S. provisional application 60/231,394, filed Aug. 5, 2009.

BACKGROUND OF THE INVENTION

1. Field of the Invention

The subject of the invention is a method for purifying the rabies virus that has been obtained from a culture of cells.

2. Summary of the Related Art

In general, virus harvests obtained from infected cell cultures contain not only the desired viruses, but also the proteins and the DNA of the cells, which are impurities which should be removed. The amounts of cellular proteins and DNA released are all the greater if the viruses are responsible for considerable cell lysis and/or if the viral harvests are carried out late. In addition to the impurities of cellular nature, the proteins of the medium containing the infected cells are also impurities that are also intended to be removed during the implementation of the viral purification process.

When the viruses are used to manufacture vaccines, it is advisable to obtain preparations which are as pure as possible so as to prevent the development of allergic reactions against the protein impurities. There are also countries that limit the maximum authorized amount of cellular DNA in vaccines comprising products obtained from continuous cell lines to 100 pg/vaccine dose or even less.

Various methods for purifying the rabies virus have already been described in the prior art:

U.S. Pat. No. 4,664,912 describes a method for purifying the rabies virus by zonal centrifugation after it has been inactivated with β-propiolactone. Another method consists in combining size exclusion chromatography and anion exchange chromatography when the volume of the harvest of virus to be purified is large.

U.S. Pat. No. 4,725,547 describes a method for purifying the rabies virus by affinity chromatography on cellulofine sulfate (a sulfuric acid ester of cellulose).

WO 97/06243 describes a method for purifying viruses, in particular the rabies virus, from a culture of infected Vero cells. The method comprises anion exchange chromatography followed by cation exchange chromatography and is completed by metal-binding affinity chromatography. Using this method, the amount of residual DNA contained in one vaccine dose is ≤30-40 pg, using the "Threshold Total DNA assay" technique.

Kumar A. P et al., in Microbes and Infection (2005) 7; 1110-1116, have compared two methods for purifying the rabies virus from a culture supernatant of infected Vero cells that were cultured in a medium containing fetal calf serum. It shows that the purification method based on the use of an anion exchange chromatography column (DEAE-sepharose CL-6B) is more effective than the method of purification by zonal centrifugation on a sucrose gradient, since, at a comparable degree of purity in terms of amount of residual proteins and nucleic acids, the rabies virus yield is better with the chromatographic method. Frazatti-Gallina N. M., in Vaccine (2004) 23; 511-517, has also described a method for purifying the rabies virus from a culture supernatant of infected Vero cells that were cultured in a medium free of fetal calf serum. The purification method also implements a step of anion exchange chromatography on a DEAE-cellulose-based support, after a step of clarifying and concentrating the viral harvest. Using this method, the amount of residual DNA measured by slot/blot hybridization technique is <23 pg per vaccine dose.

Thus, when the method for purifying the rabies virus comprises an ion exchange chromatography step, there is virtually systematically an anion exchange chromatography step so as to retain the nucleic acids of the medium containing the virus to be purified, on the chromatographic support.

SUMMARY OF THE INVENTION

A particularly effective virus purification method should make it possible to optimally remove the protein impurities and the cellular DNA while at the same time guaranteeing a maximum yield of purified rabies virus, and there still exists the need to find new methods which meet these requirements.

One objective of the invention is to provide a new purification method which meets these requirements.

Another objective of the invention is to provide a purification method which is suitable for purifying the rabies virus from a harvest which is free of animal serum or of serum protein and in particular to provide a purification method in which every step is carried out by means of products of non animal origin.

To this effect, a subject of the present invention is:

A method for purifying the rabies virus, comprising a single ion-exchange chromatography step, said step being cation exchange chromatography according to which:

a. the supernatant of a culture of cells infected with this virus is brought into contact with a cation exchange chromatography support comprising a polymethacrylate matrix onto which sulfoisobutyl groups are grafted by covalent bonding such that the rabies virus binds to this support, and, secondly;

b. the virus is eluted from its support.

According to one aspect of the method according to the invention, the culture supernatant of cells infected with the rabies virus is free of animal serum or free of any serum protein.

According to another aspect, the culture supernatant of cells infected with the rabies virus is free of any exogenous protein of animal origin.

According to a still another aspect, the culture supernatant of cells infected with the rabies virus, which is free of any exogenous protein of animal origin, contains exogenous proteins of non animal origin at a concentration ≤15 mg/l.

According to another aspect, the culture supernatant of cells infected with the rabies virus is free of any exogenous product of animal origin.

According to a still another aspect, the culture supernatant of cells infected with the rabies virus does not contain proteins having a molecular weight above 10 kDa.

In one embodiment of the method according to the invention, the culture supernatant of cells infected with the rabies virus is clarified before it is brought into contact with the cation exchange chromatography support.

Typically, the purification method according to the invention is characterized in that the amount of virus measured in the eluate corresponds to at least 70%, and preferably to at least 80% of the amount of virus measured in the supernatant that was brought into contact with the chromatographic support.

More particularly, the purification method is characterized in that the amount of total proteins measured in the eluate corresponds to less than 40% of the amount of total proteins measured in the supernatant that was brought into contact with the chromatographic support and in that the amount of DNA measured in the eluate corresponds to less than 5%, preferably to less than 2.5%, and even more preferably to less than 1% of the amount of DNA measured in the supernatant that was brought into contact with the chromatographic support.

In another embodiment of the method according to the invention, after having eluted the virus from its chromatographic support, the eluate is optionally concentrated and then treated with a nuclease.

In one particular aspect, the nuclease is an endonuclease.

In another embodiment of the invention, the method comprises an additional step of purifying the rabies virus, according to which the eluate treated with a nuclease is then subjected to an ultracentrifugation on a sucrose gradient and the fraction(s) of the gradient which contain(s) the purified virus is (are) recovered.

In another aspect of the invention, the purified rabies virus is then inactivated by means of a viral inactivation agent.

In one particular aspect, the viral inactivation agent is β-propiolactone.

In a further aspect, all the steps of the method according to the invention are carried out by means of products of non animal origin.

A subject of the invention is also a method for the manufacture of a rabies vaccine, according to which:
a) a culture of cells is infected with the rabies virus,
b) the rabies virus is purified from the infected-cell culture supernatant that is recovered at the end of step a) according to a method of the invention,
c) the suspension of purified virus obtained in b) is mixed into a storage buffer, and,
d) the suspension of purified virus obtained in c) is divided up in the form of single-dose or multidose vaccines.

According to another aspect, it is a method for the manufacture of a rabies vaccine, according to which:
a) a culture of cells is infected with the rabies virus,
b) the rabies virus is purified from the infected-cell culture supernatant that is recovered at the end of step a) according to a method of the invention,
c) the suspension of purified virus obtained in b) is mixed into a lyophilization buffer,
d) the mixture obtained in c) is divided up in the form of single-dose or multidose vaccines, and
e) the vaccine doses are lyophilized.

Finally, a subject of the invention is a vaccine containing purified and inactivated rabies virus, characterized in that the amount of residual DNA measured by quantitative PCR and the amount of total proteins which are present in one effective dose of vaccine (or in one dose of vaccine which contains 2.5 IU determined according to European Pharmacopeia monograph 0216 ("Rabies Vaccine for Human Use Prepared in Cell Cultures")) are, respectively, less than 20 pg and less than 40 μg, and preferably less than 10 pg and less than 20 μg.

Preferably, at least 70% of the total proteins that are present in one effective dose of vaccine are rabies virus proteins.

More preferably the vaccine is free of any exogenous product of animal origin.

DETAILED DESCRIPTION OF THE INVENTION

The method for purifying the rabies virus according to the invention comprises a single ion exchange chromatography step, said chromatographic step being a cation exchange chromatography. In the scope of the present invention, it is however well understood that the method of purifying rabies virus is not limited to only one chromatography step, but may include one or several additional steps, provided that the additional steps are not ion exchange chromatography. Contrary to what the prior art leads one to envision, the inventors have demonstrated that the performance levels of a cation exchange chromatography, the support of which comprises a polymethacrylate matrix onto which sulfoisobutyl are grafted by covalent bonding are better than those of an anion exchange chromatography. Without wishing to be bound by theory, it seems that the rabies virus has a double, positive and negative, polarity which enables it to bind both to anion exchange supports (of the DEAF type) and to a strong cation exchange supports (of the $SO_3^-$ type). For the purpose of the invention, the "performance levels of a chromatography" are calculated on the basis of the amount of rabies virus and of DNA that are found in the eluate compared with the initial amount of virus and of DNA that were brought into contact with the chromatographic support, within the loading capacity limits of the chromatographic support. At equivalent amounts of virus and of DNA that were brought into contact with the chromatographic support, the higher the amount of virus found in the eluate and the smaller the amount of residual DNA, the better the performance level of the chromatographic support. Sulfoisobutyl groups are grafted onto the polymethacrylate matrix through flexible polymeric chains which facilitate the interaction between the rabies virus and the cation exchanger. Preferably, the polymeric chain is made of a chain of monomer units having the following formula:

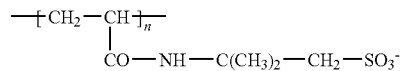

These polymeric chains are obtained by graft polymerization of a monomer having the following formula $CH_2=CH-CO-NH-C(CH_3)_2-CH_2-SO_3^-$ onto the polymethacrylate matrix-based support in presence of a cerium-based catalyst. The mean length of the polymeric chains is generally between 15 and 25 monomer units. The chromatographic support is conventionally in the form of particles, the size of which generally ranges between 20 and 100 μm, preferably between 40 and 90 This type of support is in particular sold by MERCK under the name Fractogel® EMD SO3⁻ (type M). This type of support is placed in a chromatography column, the length and diameter of which are chosen according to the volume of harvest to be purified. The results presented in example 1 show that the performance levels of the tests carried out on anion exchanger chromatographic supports and on cation exchanger chromatographic supports are mediocre from the viewpoint of those that can be obtained with the Fractogel® EMD $SO_3^-$ support. Surprisingly, except for the chromatography carried out on a Fractogel® EMD $SO_3^-$ support, the virus yields obtained with all the other cation exchanger chromatographic supports tested are very low (less than 10% of the amount of virus brought into contact with the support is found in the eluate). The virus yields obtained with anion exchanger chromatographic supports are better (between 40 and 70%) but are nevertheless lower than the virus yield obtained with a Fractogel® EMD $SO_3^-$ support, which is higher than 70% and generally higher than 80%. Therefore, the performance levels are particularly good when a strong cation exchanger chromatographic support comprising a polymethacrylate matrix onto which sulfoisobutyl groups (which play the role of ligands) are grafted by covalent bonding is used. A ready-for-use macroporous charged membrane, where the sulfoisobutyl groups are grafted onto a polymethacrylate membrane, may also be used as support.

Both more than 60% of the total proteins, and at least 2.5 $\log_{10}$ of DNA, preferably at least 3.0 $\log_{10}$ of DNA and even more preferably at least 3.5 $\log_{10}$ of DNA (which corresponds to the removal of more than 99% of the cellular DNA) are removed in a single cation-exchange chromatography step according to which the support comprises a polymethacrylate matrix onto which sulfoisobutyl groups are grafted by covalent bonding, while at the same time conserving a rabies virus yield of at least 70% (i.e. there is in the eluate an amount of rabies virus which corresponds to at least 70% of that which was initially brought into contact with the chromatographic support). These performance levels are observed in particular when the culture supernatant of cells infected with the rabies virus does not contain animal serum or serum protein (which corresponds to any protein component of the serum, like albumin). Therefore, the amounts of total proteins and of DNA measured in the chromatographic eluate contains, respectively, less than 40% of the amount of total proteins present in the volume of culture supernatant of cells infected with the rabies virus and less than 5%, preferably less than 2.5%, and even more preferably less than 1% of the amount of DNA also present in the volume of supernatant that was brought into contact with the chromatographic support. On the other hand, at least 70% of the amount of rabies virus present in the volume of supernatant that was brought into contact with the chromatographic support is found in the eluate.

For the purpose of the invention, the "total proteins" means all the proteins that are present in the material that is analyzed. They are represented by the rabies virus proteins, the cellular proteins, the proteins of the cell culture medium and of the viral infection medium and also possibly by the proteins that are possibly introduced during the purification process (for instance benzonase). The cellular proteins, the proteins of the culture medium and of the viral infection medium as well as the proteins that are possibly introduced during the purification process are the impurities (protein impurities) that are intended to be removed, whereas the intention is to conserve as much as possible the proteins of the rabies virus. The rabies virus proteins are glycoprotein G, nucleoprotein N, Phosphoprotein P, matrix protein M, and RNA dependant RNA polymerase L.

The amount of rabies virus is evaluated on the basis of the measurement of the rabies virus glycoprotein G under a form correctly folded. This is usually carried out by means of a "sandwich" ELISA method with the use of two antibodies that recognizes at least one, or preferably two conformational epitopes of the glycoprotein G, as it is described in example 1. A rabies virus neutralizing antibody recognizing a conformational epitope located on the antigenic site II of glycoprotein G (Journal of Clinical investigation (1989), vol. 84, pp. 971 to 975) is used as capture antibody, and a rabies-virus-neutralizing antibody recognizing a conformational epitope located on the antigenic site III of glycoprotein G (Biologicals (2003), vol. 31, pp. 9 to 16) is used as revealing antibody. The results are expressed in IU on the basis of the use of a reference standard which has been calibrated with respect to the NIBSC international reference.

The Bradford method, which is well known to those skilled in the art, is used to measure the amount of total proteins.

To measure the amount of DNA, a quantitative PCR (qPCR) method based on the quantification of a DNA fragment of the cell genome is preferably used (a DNA fragment which is repeated many times in the cell genome is preferably targeted). When the rabies virus is produced from Vero cells, the quantification of the residual DNA during the virus purification process is based on the quantification of the African green monkey alpha-satellite DNA fragment after PCR amplification using a method similar to that which is described by Lebron J. A. et al., in Developments in Biologicals (2006), vol 123, pp. ☐135-44, and details of which are given in example 1. This method is very advantageous since it makes it possible to measure all the cellular DNAs which have more than 200 base pairs.

The culture supernatant containing the rabies virus is produced from a cell culture that has been infected with the rabies virus. Any cell culture in which the rabies virus replicates is suitable for the subject of the invention. These cultures may be primary cultures of animal tissues, such as primary chicken embryo cultures (for example, primary chicken embryo fibroblast (PCEF) cultures), primary cultures of neonate mouse brains, or primary monkey, rabbit, hamster or dog kidney cultures, but a cell culture originating from established cell lines that derive from primary cultures of animal tissues is preferably used. The lines are in particular cell lines originating from primates, such as the VERO, WI-38, MRC5, PERC.6 line or the 293 line, from horses, from cows (such as the MDBK line), from sheep, from dogs (such as the MDCK line), from cats or from rodents (such as the BHK21, HKCC or CHO line). Particularly preferably, the Vero cell line is used, said line having many advantages: it is a continuous line that can be readily cultured on the industrial scale, which has a very weak mutagenic capacity and which is very sensitive to the rabies virus.

The cells can be cultured in suspension or on a support depending on whether or not they have adhesion properties, in a batch or a fed batch mode or according to a continuous perfusion culture mode. In the case of cell line culture on the industrial or semi-industrial scale, biogenerators are generally used, the volume of which is greater than 10 liters and may go up to more than 2000 liters, comprising a stirring system, a device for injecting a $CO_2$ gas stream and an oxygenation device. They are equipped with probes which measure the internal parameters of the biogenerator, such as the pH, the dissolved oxygen, the temperature, the pressure of the tank, or certain physicochemical parameters of the culture (such as the consumption of glucose or of glutamine or the production of lactates and of ammonium ions). The pH, oxygen and temperature probes are connected to a bioprocessor which continually regulates these parameters. In the case of adherent cell lines cultured in biogenerators, the culture medium contains microcarriers which are microbeads to which the cells attach. These microcarriers are kept in suspension by mechanical stirring, or by means of a gas stream. In the case of the Vero cell line, use is normally made of microcarriers, of which the adhesive electrostatic matrix is based on dextran substituted with N,N-diethylaminoethyl groups, which are sold in particular by Amersham Biosciences under the name Cytodex 1 or Cytodex 2. Cytodex 3 microbeads sold by Amersham Biosciences may also be used as microcarriers.

The medium which is used for culturing the cells, also known as cell culture medium, may or may not be supplemented with serum of animal origin, or contain one or more serum proteins such as human albumin, or be free of any protein of animal origin, or even be free of any protein. Usually, a cell culture medium free of animal serum or even free of any serum protein like albumin that may be responsible for the development of a hypersensitivity reaction in the vaccinated individual is used (Swanson M. C. et al., Journal of Infectious Disease (1987); 155(5):909-913). Preferably, a culture medium free of any protein of animal origin or even better free of any product of animal origin is used. The term "protein or product of animal origin" means a protein or a product, of which the manufacturing process comprises one or several steps in which a material originating from animals or humans is used. This makes it possible to decrease the risks of transmission of diseases such as BSE which may be linked to the use of biological products of animal origin. The culture media contain generally small amounts of proteins in the form of recombinant proteins or proteins extracted from plants (soya, rice, etc. . . . ). They commonly contain low molecular-weight proteins (≤10 kDa) at low concentrations. Usually, the concentration of total proteins in these media is ≤15 mg/l measured by the Bradford method. This is the case in particular of the VP SFM medium sold by Invitrogen, which is suitable for the process according to the invention, in particular for cultivating Vero cells. Mention is also made of the media Opti Pro™ serum-free (InVitrogen), Episerf (In-Vitrogen), Ex-cell® MDCK (Sigma-Aldrich), Ex-Cell™ Vero (SAFC biosciences), MP-BHK® serum free (MP Biomedicals), SFC-10 BHK express serum free (Promo cell), SFC-20 BHK express protein free (Promo cell), HyQ PF Vero (Hyclone Ref. SH30352.02), Hyclone SFM4 Megavir, MDSS2 medium (Axcell biotechnology), Iscove's modified DMEM medium (Hyclone), Ham's nutrient media (Ham's-F10, Ham's-F12), Leibovitz L-15 medium (Hyclone), which are free of any product of animal origin and which contain low amounts of proteins (≤15 mg/l).

The rabies virus may come from any origin provided that it reproduces in rabies virus-sensitive cells. Rabies virus strains which have been established from primary isolates are generally used, such as the Pasteur 2061 strain, the VP-11 strain or the Pitman-Moore 1.503-3 M strain. These very virulent strains are intended for the manufacture of inactivated rabies vaccines. Use may also be made of rabies virus strains that have been attenuated for the purpose of producing a live attenuated rabies vaccine. They are, for example the SAD Bern strain or the SAD B19 strain or strains derived therefrom, such as the SAG1 and SAG2 strains that derive from the SAD Bern strain owing to the existence of point mutations in the rabies virus glycoprotein G (EP 350398, EP 583998). EP 1253 197 also describes other, more stable, attenuated rabies virus strains, which comprise one or more point mutations in the rabies virus phosphoprotein P and glycoprotein G.

The culture supernatant of the cells infected with the rabies virus is obtained using a viral infection medium, which replaces the cell culture medium at the time of the infection of the cells and which serves for the production of the rabies virus by the infected cells. The chemical composition of the viral infection medium may be identical to or may be different than the composition of the cell culture medium. The viral infection medium, like the cell culture medium, may be supplemented with serum of animal origin or with one or more serum proteins, but a viral infection medium free of animal serum or free of any serum protein is preferably used. Preferably, a viral infection medium free of any protein of animal origin or even better free of any product of animal origin is used to decrease the risks of transmission of diseases such as BSE which may be linked to the use of biological products of animal origin. It contains generally small amounts of proteins in the form of recombinant proteins or proteins extracted from plants (soya, rice, etc. . . . ). Commonly, it contains low molecular-weight proteins (≤10 kDa) at low concentrations. Usually, the concentration of total proteins in such medium is ≤15 mg/l measured by the Bradford method. As medium free of any product of animal origin and that contains low amounts of proteins (≤15 mg/l), mention is made of VP SFM medium (Invitrogen), Leibovitz L-15 medium, MEM medium (Sigma-Aldrich), Hyclone SFM4 Megavir™ medium (Hyclone) or, optionally, one of the media based on plant extracts as described in application WO 99/4768. For example, when the rabies virus is produced from a Vero cell culture, the infected-cell culture supernatant is generally obtained by using a medium free of any serum protein or even free of any product of animal origin. Depending on the composition of the cell culture medium and of the viral infection medium, the infected-cell culture supernatant may advantageously be:

free of any serum protein, and/or free of any exogenous protein of animal origin, and/or free of any exogenous product of animal origin.

When the infected-cell culture supernatant is free of any exogenous protein of animal origin or is free of any exogenous product of animal origin, the exogenous proteins of non animal origin that are present in the supernatant are preferably at a low concentration (≤15 mg/l) measured by the Bradford method.

The term "exogenous protein or exogenous product" means any protein or product that is not a component of the rabies virus or of the cells used for the production of rabies virus. Exogenous proteins or exogenous products are components that are introduced during the production and/or the purification of rabies virus. For instance, the proteins or the products that are optionally present in the medium composition, the enzymes such as trypsin or benzonase that are introduced during the production and/or the purification of rabies virus are exogenous proteins or exogenous products. The exogenous proteins/products are of animal origin when their manufacturing process comprises one or several steps, in which a material originating from an animal or from a human is used. The exogenous proteins/products are of non animal origin when they are produced by other means, for example by using a plant material, by chemical synthesis or by genetic recombination using yeasts, bacteria or plants.

The harvesting of the culture supernatants containing the infectious virus generally begins 2 to 3 days after having infected the cells, and continues for about two weeks since the virus is not very lytic. After each harvest, the infected cells are put back in culture with new viral infection medium. The proteins that are found in the culture supernatants are of cellular and viral origin but also originate from the viral infection medium and to a minimal extent originate from the cell culture medium. It is possible to store all the harvests, or to keep only the harvests which have very high infectious titers. The harvests can be stored individually. It is also possible to mix several harvests. The harvests are normally kept at a temperature about +5° C. or in frozen form.

As a precaution, the culture supernatant containing the virus to be purified is often clarified before the cation exchange chromatography step so as to remove the coarse cell debris, the aggregates possibly present, and the residual microcarriers when the cell culture has been carried out on microcarriers. Any clarification method well known to those skilled in the art may be used in the method according to the invention. It is possible, for example, to centrifuge the supernatants or to perform size exclusion chromatography in order to clarify the culture supernatant. The clarification is usually carried out by tangential and/or frontal membrane filtration and/or depth filtration using one or more filters, the porosity of which usually ranges between 0.2 and 1.5 μm, preferably between 0.4 and 1.0 μm. The clarification can be carried out by means of a single filtration of the culture supernatant in cases where there is little debris and few aggregates. The clarification can also be carried out by combining at least two successive filtrations, the first filtration being carried out, for example, with a relatively coarse filter having, for example, a porosity of between 0.3 and 1.5 µm, while the second filtration is carried out with a relatively fine filter having, for example, a porosity of between 0.2 and 0.5 µm. It is also possible to provide for a prefiltration step, beforehand, using a prefilter with a large porosity (between 2 and 10 µm) in order to remove the large debris. As filters that are suitable for the object of the invention, mention may be made of cellulose filters, regenerated cellulose fibers, cellulose fibers combined with inorganic filters (for example, based on diatoms, on perlite or on fumed silica), cellulose filters combined with inorganic filters or organic resins, or polymer-based filters, such as, for example, nylon, polypropylene, fluorinated polyvinylidene or polyethersulfone filters. These filters are in particular sold under the name Durapore®, Millipak® or Millidisk™ distributed by the company Millipore or the filters distributed by the company Pall. As depth filter system, mention may be made of the depth filters of the AP series (AP01), of the CP series (CP10, CP30, CP50, CP60, CP70, CP90), of the HP series (HP10, HP30, HP50, HP60, HP70, HP90), of the CA series (CA10, CA30, CA50, CA60, CA70, CA90) and of the SP series (SP10, SP30, SP50, SP60, SP70, SP90), which are supplied by the company CUNO, the CUNO Delipid and Delipid Plus filters, and the depth filters of the CE series (CE15, CE20, CE25, CE30, CE35, CE40, CE45, CE50, CE70, CE75) and of the DE series (DE25, DE30, DE35, DE40, DE45, DE50, DE55, DE60, DE65, DE70, DE75), which are supplied by the company Millipore corp., the filters of the HC series (A1 HC, B1HC, COHC) and the Clarigard and Polygard filters from the company Millipore corp. As another filtration system, mention may also be made of the depth filters distributed by ManCel associates (for example, PR 12 UP, PH12, PR 5 UP) or the filters from PALL or from the company SeitzShenk Inc (for example, Bio20, SUPRA EKIP, KS-50P). Advantageously, the clarification step may be carried out by means of a filter capsule comprising two membranes with different porosities, which amounts to carrying out two successive filtrations in a single step. The Sartopore-2 filter capsules sold by Sartorius, comprising a 0.8 µm membrane and a 0.45 µm membrane, are very suitable for clarifying the culture supernatant. A prefiltration step as indicated above may also be incorporated beforehand, as required.

Irrespective of whether or not the culture supernatant is clarified, it is if required adjusted to a pH of between 7 and 8, preferably between 7.0 and 7.6. It is also verified that the conductivity is ≤20 mS/cm, preferably between 10 and 20 mS/cm, and particularly preferably between 14 and 18 mS/cm. The culture supernatant is then introduced into a cation exchange chromatography column, the support of which is constituted of particles of Fractogel® EMD SO3⁻ (type M) and the dimensions of which are suitable for the volume of supernatant to be purified. The column is pre-equilibrated in a low-ionic-strength equilibation buffer (≤200 mM). The column is then washed with a washing buffer which generally has the same composition as the equilibration buffer. What leaves the column is mainly the protein impurities and the nucleic acids. The virus which has been retained on the column is then eluted using an elution buffer, the ionic strength of which is at least 400 mM. By way of example of buffer solutions suitable for the object of the invention, mention may be made of 20 mM Tris buffer containing 150 mM NaCl, pH=7.5, for equilibrating and washing the column, and 20 mM Tris buffer containing 600 mM NaCl, pH=7.5, as virus elution buffer, but any other equivalent buffer solution could also be suitable. The loading capacities of the column being respected, more than 70% of the amount of virus that was initially introduced in the column is thus recovered in the eluate, while the amounts of DNA and of total proteins recovered in the eluate represent, respectively, less than 5% and less than 40% of the initial amounts of DNA and of total proteins that were initially introduced in the column. These results are obtained in particular when the infectious culture supernatants do not contain serum of animal origin or do not contain serum protein or contain exogenous proteins of non animal origin at low concentration (≤15 mg/l).

The inventors have also shown that, by combining a cation exchange chromatography step on a support comprising a polymethacrylate matrix onto which sulfoisobutyl groups are grafted with an enzymatic nucleic acid digestion step, it is also possible to reduce the level of residual DNA by approximately a further 1.5 to 2 $Log_{10}$, to such an extent that, by combining these two steps, at least 4.0 $log_{10}$ of DNA are successfully removed. By way of comparison, using a method for removing nucleic acids based on an enzymatic nucleic acid digestion that is repeated twice, a level of DNA removal which does not exceed 3.5 $log_{10}$ is obtained, the second digestion not enabling the residual level of DNA to be reduced beyond a further 0.5 to 1 $Log_{10}$ (see example 2). As enzymatic agent for nucleic acid digestion, use may be made of one or more enzymes, preferably an RNAse and/or a DNAse, or a mixture of endonucleases known to those skilled in the art, for instance Pulmozyme™. In the context of the method according to the invention, Benzonase™, preferably obtained by genetic recombination, is generally used, in a concentration range of generally between 1 and 50 U/ml. It is an endonuclease which acts by rapidly cleaving cellular DNA and ARN and which reduces the viscosity of the medium. The temperature and the duration of the enzymatic treatment are parameters that can be easily controlled by those skilled in the art and that depend on the initial concentration of the endonuclease in the reaction medium. To prevent any aggregation phenomenon, a very small amount of a surfactant, which is preferably nonionic, such as poloxamer 188 (Pluronic F 68) can be added, at a very low concentration, to the chromatographic eluate. Prior to the enzymatic treatment step, the eluate may optionally be concentrated when the volume is large. The concentration step is generally carried out by ultrafiltration on a membrane, having a cutoff threshold of between 100 kDa and 300 kDa, preferably between 100 kDa and 200 kDa. Ultrafiltration is characterized by a tangential flow over the membrane which induces a force that enables the molecules to diffuse through the porous membrane. The flow imposed by a recirculation pump is divided up into two components: the recirculation flow which performs the sweep (or retentate flow) and the filtrate (permeate) flow which passes through the membrane. The composition of the membrane may, in a nonlimiting manner, be made of regenerated cellulose, of polyethersulfone, of polysulfone or of derivatives of these products. It may be in the form of flat sheets inside cassettes (in particular for tangential ultrafiltration) or of hollow fibers. The membranes are in particular sold by Pall under the name Omega™, by Millipore under the name Biomax™ membranes and by Sartorius under the name Sartocon®. A back-pressure may also be applied on the filtrate (permeate) side in order to reduce the transmembrane pressure, as is described in WO 2006/108707. As the eluate passes through the membrane, the volume of the eluate decreases and the virus that does not pass through the membrane is concentrated. When the eluate is ultrafiltered, the volume thereof can be decreased by a factor that may range from 1 to 100, or even 150, thus making it possible to obtain the desired final volume. This concentration step may be completed with a diafiltration step which makes it possible to modify the composition of the buffer without however modifying the volume of the retentate. This is recommended when the composition of the buffer in the retentate, owing to the decrease in volume of the eluate, is no longer compatible with good enzymatic activity of the endonuclease. A buffer, the composition of which is compatible with good enzymatic activity of the endonuclease, is then added to the retentate recirculation flow. By way of example, and without being restrictive in nature, mention is made of buffer compositions compatible with good enzymatic activity of an endonuclease such as Benzonase™: they contain a Tris buffer in a concentration range by molarity of from 10 to 50 mM, $MgCl_2$ in a concentration range of generally from 1 to 10 mM and, optionally, another salt, such as NaCl, in a concentration range of from 100 mM to 600 mM, the pH of these buffer solutions being in a pH range of from 7.0 to 8.0. As indicated above, the eluate recovered after the chromatographic step may also be treated directly with an endonuclease, such as Benzonase™ by adding $MgCl_2$ in a concentration range of generally from 1 to 10 mM before the addition of Benzonase.

In order to complete the removal of the protein impurities, and in particular the removal of Benzonase, the eluate which has been treated with an endonuclease is subjected to a sucrose-gradient ultracentrifugation step, it being possible for this ultracentrifugation step to be repeated one or more times. The ultracentrifugation enables the rabies virus to be isolated by adjusting the difference in sedimentation coefficient between the various entities present in the eluate: the protein impurities migrate into the low sucrose densities (≤35% of sucrose), whereas the rabies virus is in the higher sucrose densities (≥35% of sucrose). The sucrose-gradient ultracentrifugation step is generally carried out according to the "continuous flow" method when the volumes to be treated are large or in a rotor when the volumes are relatively small. The sucrose-gradient ultracentrifugation is usually carried out on "sucrose cushions" at a temperature about 5° C. The eluate which has been treated with an endonuclease may be in a nonconcentrated form or in a form concentrated 10 times, 20 times, 50 times, 100 times, 150 times, or even more. The ratio between the total volume of the eluate to be ultracentrifugated and the total volume of the sucrose gradient is usually between 0.5 and 2.0, and preferably between 0.5 and 1.5. The density of the low-density sucrose "cushion" is usually within a range of from 10% to 35% w/w, while the density of the high-density sucrose "cushion" is usually within a range of from 40% to 60% w/w. The volume of low-density sucrose is generally greater than the volume of high-density sucrose, all the more so if the volume of the eluate subjected to the ultracentrifugation step is large. The ratio between the volume of high-density sucrose and the volume of low-density sucrose is usually between 0.3 and 0.7. The duration of the ultracentrifugation depends on the ultracentrifugation speed, which is in general ≥30000 g. An ultracentrifugation time of 2 hours is generally sufficient when the ultracentrifugation speed is ≥65000 g. After ultracentrifugation, the product distributed within the gradient is taken off using a peristaltic pump and fractionated. The amount of sucrose contained in each fraction is measured using a refractometer. In each fraction, the amount of rabies virus is measured, on the basis of assaying the glycoprotein gpG by ELISA, as well as the amount of total proteins by the Bradford method. The separation profile is thus established. At the end of these analyses, the fractions of the gradient containing essentially the rabies virus are selected and combined. During this step, more than 85% and preferably more than 90% of the total proteins are removed, this being essentially protein impurities since the rabies virus yield is ≥70% and preferably ≥80%.

Thus, when the step of clarification of the infected-cell culture supernatant, the step of cation exchange chromatography on a support comprising a polymethacrylate matrix onto which sulfoisobutyl groups are grafted by covalent bonding, optionally followed by a concentration and/or diafiltration step, the step of treatment with an endonuclease and the step of sucrose-gradient ultracentrifugation are combined in the purification method according to the invention, a composition of purified rabies is obtained which, for an amount of rabies virus corresponding to 4.5 IU (on the basis of measuring gpG by ELISA) or to one effective dose of vaccine, contains less than 50 pg of residual DNA, preferably less than 20 pg of residual DNA and even more preferably less than 10 pg of residual DNA (measured by qPCR) and contains less than 40 µg of total proteins, preferably less than 20 µg of total proteins (measured by the Bradford method). Usually, at least 70% of the total proteins are viral proteins. The overall yield of purified virus is at least 45%, and preferably at least 50%, and even more preferably at least 60%. The overall yield of purified virus is calculated on the basis of the ratio of the amount of virus present in the gradient fraction(s) recovered after ultracentrifugation to the amount of virus initially present in the volume of infected-cell culture supernatant to be purified. Preferably, the rabies virus infected-cell culture supernatant is free of any serum protein, or free of any exogenous protein of animal origin, or even free of any exogenous product of animal origin to warrant in particular a better biological safety of the vaccine composition.

By way of example, table I below indicates, for each step of the method for purifying the rabies virus from a culture supernatant of infected Vero cells, the amounts of virus recovered and also the amounts of DNA and of proteins removed.

TABLE I

Table summarizing the various steps of the rabies virus purification process with the associated virus yields and the amounts of DNA and of proteins removed.

| Step | Amount of virus recovered (as %)* | | Amount of proteins removed (as %)** | | Amount of DNA removed (en $\log_{10}$)*** | |
|---|---|---|---|---|---|---|
| | in the step | overall | in the step | overall | in the step | overall |
| Clarification | 90 | 90 | ND | ND | ND | ND |
| Chromatography on EMD/$SO_3^-$ support | 89 | 80 | 60 | 60 | ND | ND |
| Ultrafiltration/diafiltration | 97 | 77 | 18 | 67 | 2.7 | 2.7 |
| Benzonase treatment + sucrose-cushion ultracentrifugation | 70 | 54 | 88 | 96 | 1.6 | 4.3 |

*the amount of rabies virus is determined on the basis of assaying the rabies virus glycoprotein G by ELISA according to the method described in example 1.
**the amount of total proteins is measured by the Bradford technique.
***the amount of DNA is measured by qPCR according to the method described in example 1.
ND: Not determined The purified rabies virus recovered after the ultracentrifugation step is generally in a form that is too highly concentrated and that is often diluted so as to prevent the formation of viral aggregates during storage. A phosphate buffer at a pH of approximately 8, optionally supplemented with a saline solution, for instance a sodium chloride solution, is normally used as dilution buffer. Thanks to the process according to the invention, the suspension of purified rabies virus obtained can be used as live or attenuated virus vaccine or as inactivated virus vaccine. When the vaccine is intended for human medicine, the suspension of purified rabies virus is generally inactivated.

Viral Inactivation Step

The method for purifying the rabies virus as described in the invention ends with a viral inactivation step when the virus is intended for the manufacture of an inactivated vaccine. The viral inactivation can be carried out by means of chemical agents well known to those skilled in the art, such as formaldehyde, glutaraldehyde or β-propiolactone. It is also possible to use the inactivation method as described in WO 2005/093049, which consists in bringing the purified viral solution into contact with a photoactivatable hydrophobic compound and in exposing this mixture to light. Among the photoactivatable hydrophobic compounds, mention is made of azidobenzene, 1-azidonaphthalene, 4-azido-2-nitro-1-(phenylthio)benzene, 1-azido-4-iodobenzene, 1-azido-5-iodonaphthalene, 3-phenyl-3H-diazirene, 3-phenyl-3-(trifluoromethyl)-3H-diazirene, 3-(3-iodophenyl)-3-(trifluoromethyl)-3H-diazirene, 1-azidopyrene, adamantine diazirene, 12-(4-azido-2-nitrophenoxy)stearic acid, w-(m-diazirinophenoxy) fatty acid, 12-[(azidocarbonyl)oxy]stearic acid, 12-azidostearic acid, 11-(3-azidophenoxy)undecanoic acid or w-(m-diazirinophenoxy)undecanoic acid or 1,5-iodonaphtyl azide. Preferably, β-propiolactone (BPL) is used because it is both a viral inactivation agent and an alkylating agent resulting in cleavages in the DNA. It may therefore also contribute to reducing the level of residual DNA and to inhibiting its biological activity. The inactivation of the rabies virus is carried out by means of a solution of β-propiolactone diluted to between 1/3500 and 1/4000 (final volume concentration in the solution containing the purified virus) at a temperature of approximately 12° C. The lower the concentration of β-propiolactone, the longer the time necessary for inactivation of the virus. Generally, the inactivation of the virus is carried out in a time period ranging from 12 h to 48 h. The activity of the β-propiolactone is neutralized by simply heating the solution at a temperature of approximately 37° C. for approximately 2 h. It is then verified that the pH of the solution is >7.0. The pH is rectified, if necessary, by means of a dilute solution of sodium hydroxide, or alternatively, before the treatment with β-propiolactone, the solution containing the purified virus is buffered with a solution based on a phosphate buffer pH ~8, thereby preventing any acidification of the solution during the hydrolysis of the β-propiolactone.

The viral suspension purified according to the method of the invention is in general stored in a storage buffer such as, for example, a Tris buffer or a phosphate buffer at a pH around 8.0. Although the purified viral suspension can be mixed directly with the storage buffer, a step of diafiltration by ultrafiltration into the storage buffer is generally carried out, completed if necessary by a step of concentration if the purified virus is not sufficiently concentrated. In case an ultrafiltration step is carried out, it is advisable to use a porous membrane having a cut-off threshold of between 5 kDa and 100 kDa, preferably between 8 kDa and 50 kDa. The stock of purified virus thus prepared is finally sterilized by filtration through a membrane having a porosity ≤0.2 μm, and then stored at approximately +5° C., preferably in a frozen form before being divided up in the form of single-dose or multidose vaccines. An additional step of lyophilization of the vaccine preparations may also be included. In this case, the storage buffer composition is chosen in such a way that it can be lyophilized. The overall yield of inactivated purified virus, calculated here on the basis of the ratio of the amount of virus present in the stock of purified virus obtained after the ultimate sterilizing filtration step to the amount of virus initially present in the volume of the infected-cell culture supernatant to be purified is still at least 40%, which attests to the industrial advantage of such a method of purification.

Ultimately, a vaccine containing purified rabies virus may be produced with a very good yield and with a very high level of purity using a process according to which the steps of:
  producing a cell batch from a cell bank, usually from a working cell bank, and of,
  producing rabies virus after infection of the cell batch with a viral seed lot, and of,
  purifying rabies virus from the infected-cell culture supernatant are all carried out with the use of exogenous products of non-animal origin.

Thanks to the process of the invention a rabies vaccine may be obtained free of any exogenous product of animal origin.

Accordingly, a subject of the invention is also a process for the manufacture of a rabies vaccine, according to which:
  a) a batch of cells is produced,
  b) the batch of cells is infected with rabies virus,
  c) the rabies virus is purified from the infected-cell culture supernatant that is recovered from the infected batch of cells according to a method of the invention,
  d) the suspension of purified virus is mixed in a storage buffer, and
  e) the suspension of purified virus obtained in c) is divided up in the form of single-dose or multidose vaccines.

According to one embodiment of the vaccine manufacturing process, the storage buffer is a lyophilization buffer. In this case, the suspension of purified virus is mixed in the lyophilization buffer, the mixture is then divided up in the form of single-doses or multidose vaccines, and finally the vaccine doses are lyophilized.

In a preferred embodiment of the vaccine manufacturing process, all the steps of the process are carried out with exogenous products of non-animal origin. The vaccine is free of any exogenous product of animal origin, which increases the quality of the vaccine obtained in terms of biological safety.

Finally, a subject of the invention is a vaccine containing purified rabies virus according to which the amount of residual DNA measured by quantitative PCR and the amount of total proteins which are present in one effective dose of vaccine are less than 20 pg of residual DNA and less than 40 μg of total proteins. Preferably, one effective dose contains less than 10 pg of residual DNA and less than 20 μg of total proteins. More preferably, at least 70% of the total proteins are rabies proteins. Ultimately, the vaccine is free of any exogenous product of animal origin. The rabies virus contained in the vaccine may be inactivated or attenuated. The densitometric analysis of the electrophoretic profile of a vaccine sample, obtained after polyacrylamide gel electrophoresis and visualization with coomassie blue, in fact shows that more than 70% of the proteins are of viral origin. The five rabies proteins, i.e. envelop glycoprotein G, nucleoprotein N, Phosphoprotein P, matrix protein M, and RNA dependant RNA polymerase L are essentially found onto a SDS-PAGE (Sodium Dodecyl Sulfate-Polyacrylamide gel electrophoresis) carried out in the presence of 2-mercaptoethanol. Furthermore, the particle size analysis of a vaccine sample by means of the zetasizer Nano ZS machine (Malvern Instruments), which measures the Brownian motion of the particles on the basis of "quasielastic" light scattering (Dynamic Light scattering), shows the existence of a single population of particles of between 100 and 300 nm with an average value at 180 nm, which corresponds to the average size of the rabies virus. The analysis of a vaccine sample by electron microscopy analysis shows the presence of viral particles having the classical bullet shape of the rabies virus. The vaccine according to the invention is therefore in the form of a homogeneous suspension of whole purified rabies viruses wherein the particle size analysis by means of the Zetasizer Nano ZS machine shows the existence of a single peak between 100 and 300 nm approximately. This homogeneous suspension of purified rabies viruses with the purity characteristics as described can be obtained by implementing the purification method as described in the invention.

The official test accepted by the WHO for evaluating the effectiveness of a rabies vaccine is described in the WHO Rabies monograph (WHO Technical Series Report 941-January 2007 and European Pharmacopeia monograph 0216 ("Rabies Vaccine for Human Use Prepared in Cell Cultures"). In order to be effective, one vaccine dose should contain at least 2.5 IU determined according to European Pharmacopeia monograph 0216.

The potency of rabies vaccine according to European Pharmacopeia monograph 0216 is determined by comparing the dose necessary to protect mice against the effects of a lethal dose of rabies virus, administered intracerebrally, with the quantity of a reference preparation of rabies vaccine necessary to provide the same protection. For this comparison a reference preparation of rabies vaccine, calibrated in International Units, and a suitable preparation of rabies virus for use as the challenge preparation are necessary.

The International Unit is the activity contained in a stated quantity of the International Standard. The equivalence in International Units of the International Standard is stated by the World Health Organisation.

The test described below uses a parallel-line model with at least 3 points for the vaccine to be examined and the reference preparation. Once the analyst has experience with the method for a given vaccine, it is possible to carry out a simplified test using a single dilution of the vaccine to be examined. Such a test enables the analyst to determine that the vaccine has a potency significantly higher than the required minimum, but does not give full information on the validity of each individual potency determination. The use of a single dilution allows a considerable reduction in the number of animals required for the test and must be considered by each laboratory in accordance with the provisions of the European Convention for the Protection of Vertebrate Animals used for Experimental and other Scientific Purposes.

Selection and distribution of the test animals. Use healthy female mice, about 4 weeks old, each weighing 11-15 g, and from the same stock. Distribute the mice into 6 groups of a size suitable to meet the requirements for validity of the test and, for titration of the challenge suspension, 4 groups of 5.

Preparation of the Challenge Suspension. Inoculate mice intracerebrally with the Challenge Virus Standard (CVS) strain of rabies virus and when the mice show signs of rabies, but before they die, euthanise them, then remove the brains and prepare a homogenate of the brain tissue in a suitable diluent. Separate gross particulate matter by centrifugation and use the supernatant liquid as the challenge suspension. Distribute the suspension in small volumes in ampoules, seal and store at a temperature below −60° C. Thaw one ampoule of the suspension and make serial dilutions in a suitable diluent. Allocate each dilution to a group of 5 mice and inject intracerebrally into each mouse 0.03 ml of the dilution allocated to its group. Observe the mice for 14 days. Calculate the LD50 of the undiluted suspension using the number in each group that, between the 5th and 14th days, die or develop signs of rabies.

Determination of potency of the vaccine. Prepare 3 fivefold serial dilutions of the vaccine to be examined and 3 fivefold serial dilutions of the reference preparation. Prepare the dilutions such that the most concentrated suspensions may be expected to protect more than 50 percent of the animals to which they are administered and the least concentrated suspensions may be expected to protect less than 50 percent of the animals to which they are administered. Allocate the 6 dilutions, 1 to each of the 6 groups of mice, and inject by the intraperitoneal route into each mouse 0.5 ml of the dilution allocated to its group. After 7 days, prepare 3 identical dilutions of the vaccine to be examined and of the reference preparation and repeat the injections. 7 days after the second injection, prepare a suspension of the challenge virus such that, on the basis of the preliminary titration, 0.03 ml contains about 50 LD50. Inject intracerebrally into each vaccinated mouse 0.03 ml of this suspension. Prepare 3 suitable serial dilutions of the challenge suspension. Allocate the challenge suspension and the 3 dilutions, 1 to each of the 4 groups of 5 control mice, and inject intracerebrally into each mouse 0.03 ml of the suspension or dilution allocated to its group. Observe the animals in each group for 14 days and record the number in each group that die or show signs of rabies in the period 5-14 days after challenge.

The test is not valid unless:

for both the vaccine to be examined and the reference preparation the 50 percent protective dose lies between the largest and smallest doses given to the mice;

the titration of the challenge suspension shows that 0.03 ml of the suspension contained not less than 10 LD50;

the statistical analysis shows a significant slope and no significant deviations from linearity or parallelism of the dose-response curves;

the confidence limits (P=0.95) are not less than 25 percent and not more than 400 percent of the estimated potency.

The vaccine complies with the test if the estimated potency is not less than 2.5 IU per human dose.

The administration of one effective dose of a rabies vaccine (i.e. at least 2.5 IU) intramuscularly to humans according to the vaccination or sero-vaccination protocols normally recommended induces the development of protective immunity. Moreover, it has been observed that, when the amount of rabies virus contained in one vaccine dose according to the invention is at least 4.5 IU on the basis of the measurement of glycoprotein G by ELISA, this amount corresponds to at least one effective dose of vaccine (i.e. contains at least 2.5 IU according to the NIH test).

The effective dose of the vaccine, which is injected intramuscularly in humans, is generally contained in a volume of 0.5 to 1 ml of a liquid suspension, which is ready to use or obtained by simple thawing or else obtained extemporaneously by reconstituting a lyophilisate with a solvent.

The vaccination protocols used to protect humans against rabies are well known and differ depending on whether a preventive or curative vaccination is involved. Usually, in the case of a preventive vaccination, the prime vaccination protocol comprises two or 3 intramuscular injections of one effective dose of vaccine. The vaccination boosters are then given, at regular intervals, by administering a single effective dose of vaccine. In the case of a curative vaccination, the vaccination protocols differ depending on whether or not the individual exposed to the rabies virus has already been vaccinated and depending on the country. The vaccination protocol normally recommended in nonimmunized or poorly immunized individuals, in parallel with the administration of an antirabies serum, comprises 5 successive intramuscular injections of one effective dose of vaccine over a period of 1 month, followed by a booster at 3 months. The number of injections is reduced to 3, or even to one, when the individuals exposed to the virus have previously received a complete preventive vaccination. Other vaccination protocols in the context of curative vaccination in nonimmunized or poorly immunized individuals that make it possible to reduce the number of injections and/or amount of vaccine antigen administered can be used in the context of the present invention. These are in particular the "Zagreb" protocol, which comprises 4 intramuscular injections of one effective dose of vaccine (with 2 injections at different sites being given at day D0, followed by an injection at D7 and then at D21), or intradermal vaccination protocols.

The present invention will be understood more clearly in light of the following examples which serve to illustrate the invention without, however, limiting the content thereof.

EXAMPLE 1

Comparison of Various Chromatographic Supports in the Method for Purifying the Rabies Virus 1-1) Production of the Rabies Virus on VERO Cells in Serum-Free Medium Cells of the VERO line, after having been adapted to culture conditions in serum-free medium as described in WO 01/40443, were transferred into a 10- to 20-liter biogenerator containing cytodex 1 microcarriers in VP SFM medium (Invitrogen). After a culture period of 3 to 4 days at 37° C. with the pH being maintained at approximately 7.2±0.2, with the oxygen saturation being maintained at 25%±10% and with the medium being subjected to slight stirring, the cells were infected with rabies virus at a multiplicity of infection of 0.01 in a viral infection medium containing VP SFM medium (Invitrogen). In the case of the tests which were carried out with the Fractogel EMD-$SO_3^-$ chromatographic support, the rabies virus production was carried out on a scale of 150 liters, using 150-liter biogenerators. The infected-cell culture supernatants were harvested at days D7 (H1), D11 (H2) and D15 (H3). After each harvest, new viral infection medium was reintroduced.

1.2) Clarification and Analysis of Harvests

The clarification step was carried out using two successive frontal filtrations; the first using an 8 μm polypropylene prefilter (Sartopure PP2, SARTORIUS) which removes the few microcarriers drawn up during the harvesting, the Vero cells detached from the supports and the large cell debris; the second using an PES filter, composed of the combination of two filters, 0.8 μm and 0.45 μm (Sartopore 2, SARTORIUS), which removes the aggregates.

The amount of rabies virus present in the clarified harvests was determined by measuring the amount de glycoprotein G (gpG) measured by the following ELISA method:

Approximately 0.12 μg/100 μl of a solution of an anti-gpG monoclonal antibody 1112-1 (the characteristics of which are described in Journal of Clinical investigation (1989), volume 84, pages 971 to 975), prediluted in a coating buffer (0.2 M carbonate/bicarbonate buffer, pH 9.6), were dispensed into the wells of an ELISA microplate. After incubation overnight in a cold room, followed by several washes in a washing buffer (phosphate buffer supplemented with 0.05% Tween 20), 100 μl of a saturation buffer (phosphate buffer supplemented with 1% bovine serum albumin) were dispensed into each well. After incubation for one hour at 37° C., followed by several washes, a dilution range of each test sample was prepared in a dilution buffer (phosphate buffer supplemented with 0.05% Tween 20 and 0.1% serum albumin). In parallel, a dilution range of a reference standard, which was calibrated with respect to the international reference of the NIBSC (for example, PISRAV), was prepared in each microplate. After a further incubation for one hour at 37° C., followed by several washes, 100 μl of a solution of an anti-gpG mouse monoclonal antibody D1 (the characteristics of which are described in Biologicals (2003), volume 31, pages 9 to 16), which was biotinylated and used after dilution to 1/5000 in the dilution buffer, were dispensed into each well. The plates were left for 1 hour at 37° C. and then washed several times before dispensing 100 μl of a solution of streptavidin coupled to peroxydase (Southern Biotechnology Associates), prediluted to 1/15000 in the dilution buffer, into each of the wells. After a further incubation for one hour at 37° C., followed by several washes, 100 μl of a solution of 0.05 M citrate buffer, pH 5, containing the revealing substrate (O-phenylenediamine), were dispensed into each well. After an incubation time of 30 minutes at ambient temperature in the dark, the revealing reaction was stopped by adding 50 μl/well of a 2N solution of $H_2SO_4$. The spectrophotometric reading of the microplates was carried out at two wavelengths (492 nm and 620 nm). The optical density measured is the difference between the two readings so as to take into account the absorption by the plastic. The relative activity was calculated by the parallel lines method according to the recommendations of the European Pharmacopeia. The rabies virus titer of the sample is based on the determination of the concentration of rabies virus glycoprotein G, which is expressed in IU/ml relative to the reference.

The amount of total proteins present in the clarified harvests was measured using the conventional Bradford method sold in the form of a kit by Biorad (ref: 500-0006).

The amount of DNA present in the clarified harvests was measured by qPCR. The working protocol is similar to that which is described by Lebron J. A. et al., in Developments in Biologicals (2006), vol 123, pp. 35-44. After having extracted the residual DNA from the clarified harvests by means of the commercial Extractor kit from Wako Pure Chemicals, a fixed amount of an exogenous DNA, which serves as an internal control for the PCR amplification, was introduced into each sample. In parallel, a sample of genomic DNA originating from Vero cells lysed by successive freezings/thawings, subsequently treated with RNase A, in a proportion of 2 mg of RNase A per $2.5 \times 10^5$ cells, was prepared and then, finally, subsequently purified using the QIAamp Virus BioRobot 9604 kit (QIAGEN). The purified DNA was quantified by spectrophotometry at 260 nm. Using this purified DNA (standard DNA), a calibration range was prepared by performing 10-fold dilutions. The samples originating from the clarified harvests and also the samples of the calibration range were subsequently subjected to a cycle of PCR amplification, after having added, for each test, the fluorescent probe Alpha-MPH3, the two primers and the 2× QuantiTect Probe Master Mix premix (Qiagen) in a volume of completely nuclease-free water (qs 50 μl). The amplification cycle was carried out using the Light Cycler 480 machine (Roche Applied Science) using the program: 95° C., 15 min; 40 cycles comprising two steps 95° C., 15 sec; 60° C., 60 sec. The amount of residual DNA extracted from the clarified harvests was then calculated, by interpolation, on the basis of the measurement of the fluorescence observed compared with the calibration range established with the standard DNA. The amount of residual DNA was adjusted by a corrective factor corresponding to the charge efficiency measured for the sample by means of the quantification of the exogenous DNA. In general, the concentrations of glycoprotein G (corresponding to the rabies virus titer), of total proteins and of DNA in the clarified harvests were in ranges of from 1 to 3 IU/ml for the glycoprotein G, from 50 to 100 µg/ml for the total proteins and from 5 to 50 ng/ml for the DNA.

1.3) Measurement of the Performance Levels of Various Chromatographic Supports in Terms of their Ability to Remove Nucleic Acids and to Retain the Rabies Virus The elimination of the cellular DNA in the clarified harvests was evaluated on the following chromatographic supports:

Anionic Supports
Fractogel® EMD TMAE (Merck) (strong anion exchanger);
Fractogel® EMD DEAE (Merck) (weak anion exchanger);
Sartobind® Q positively charged membrane (Sartorius);
Mustang® Q positively charged membrane (Pall).

Cationic Support

Fractogel® EMD $SO_3^-$ (Merck) (strong cation exchanger).

Preliminary tests were carried out on the Sartobind® positively charged membrane so as to identify the best salt concentration for eluting the virus by anion exchange chromatography. These tests showed that the virus was eluted throughout the salt gradient, including at 1M. This was also true for the other anionic supports that were tested. The elution profiles obtained led us to choose a strong concentration of NaCl for eluting the maximum of virus. Since DNA began to be eluted when the NaCl concentration was around 350-400 mM, the compromise was to choose a NaCl concentration of 450 mM.

The anionic supports were subsequently equilibrated in 20 mM Tris buffer containing 150 mM NaCl, pH 7.5. The clarified harvests were then brought into contact with the various supports studied. The anionic supports were subsequently rinsed in 20 mM Tris buffer containing 150 mM NaCl, pH 7.5. The virus was subsequently detached from the support by means of a 20 mM Tris elution buffer containing 450 mM Nacl, pH 7.5.

The tests on a Fractogel column were carried out using the clarified harvest H1. Between 35 and 50 IU of rabies virus and between 13 and 25 μg of DNA were injected per ml of gel.

The tests on membrane were carried out using the clarified harvest H2. 13 IU of rabies virus and between 350 and 450 ng of DNA were injected per $cm^2$ of membrane.

The working conditions used for the cation exchange chromatography on Fractogel® EMD $SO_3^-$ Support were also optimized. The Fractogel® EMD $SO_3^-$ support was equilibrated using a 20 mM Tris buffer containing 150 mM NaCl, pH=7.5. The tests on Fractogel® EMD $SO3^-$ support were carried out using the clarified harvest H1. The conductivity of the medium (between 14 mS/cm and 18 mS/cm) and the pH (between 7.5 and 7.7) were verified. Approximately 50 IU (on the basis of the assaying of glycoprotein G) of rabies virus were injected per ml of gel. The filtrate was collected to assess the amount of virus which was not bound to the support; the support was subsequently washed in 20 mM Tris buffer containing 150 mM NaCl, pH=7.5. The virus was next eluted in 20 mM Tris buffer containing 600 mM NaCl, pH=7.5, with recovery of the viral peak in an independent fraction. The support was finally regenerated in 20 mM Tris buffer containing 1M NaCl, pH=7.5.

The results obtained are given in table II below.

TABLE II

Performance levels of the various chromatographic supports

| Characteristics of the chromatographic support | Virus yield | Residual DNA titer (ng/ml) | Amount DNA removed (as %). |
|---|---|---|---|
| Mustang Q | 47% | 4** | 93% |
| Sartobind Q | 50% | 1** | 98% |
| Fractogel EMD-TMAE | 54% | 196** | 48% |
| Fractogel EMD-DEAE | 70% | 161** | 73% |
| Fractogel EMD-SO3 | 89% | 4.15*** | 99.7%*** |

*the rabies virus titer was determined on the basis of the measurement of glycoprotein G by ELISA

**the residual DNA titer was measured by qPCR directly on the product recovered

***the residual DNA titer was measured by qPCR after concentration of the eluate by a factor of 6 by ultrafiltration.

The positively charged membrane supports (Sartobind® (Sartorius) or Mustang® Q (Pall)) facilitate the removal of the DNA (more than 90% of the DNA is removed in the fraction collected), but on the other hand, the harvested virus yields are relatively low (≤50%). With regard to the supports based on positively charged gels (Fractogel® EMD TMAE (Merck), Fractogel® EMD DEAE (Merck)), it is rather the opposite tendency that is observed, i.e. a better harvested virus yield (≥50%) but to the detriment of the removal of the DNA (73% of the DNA is removed in the best of cases). On the other hand, when the Fractogel® EMD $SO_3^-$ cationic support is used, both a very good DNA removal (more than 95% of the DNA is removed in the fraction collected) and a very good harvested virus yield (≥70%) are observed. The chromatographic performance levels of the Fractogel® EMD $SO_3^-$ cationic support are therefore better than those that are observed with the anionic chromatographic supports.

1-4) Measurement of the Chromatographic Performance Levels of Various Cationic Chromatographic Supports The previous results having shown that a strong cation exchanger support is better than an anion exchanger support we sought to define the features of the cation exchanger chromatographic support which give the best harvested virus yields. The characteristics of the strong cationic supports which were tested were the following:

Sartobind® S negatively charged membrane (Sartorius): a cellulosic membrane onto which sulfonic acid groups (ligands) are grafted;

Mustang™ S negatively charged membrane (Pall): polyethersulfone membrane onto which sulfonic acid groups (ligands) are grafted;

Capto™ S Gel (GE Healthcare): gel of which the matrix is based on agarose, onto which sulfoethyl groups are grafted through dextran spacers;

SP Sepharose XL gel (GE Healthcare): gel of which the matrix is based on agarose onto which sulfopropyl groups (ligands) are grafted through dextran spacers;

Toyopearl® SP 650 (Tosoh): gel of which the matrix is based on polymethacrylate onto which sulfopropyl groups (ligands) are grafted;

Fractogel® EMD $SO_3^-$ (Merck): gel of which the matrix is based on polymethacrylate, onto which sulfoisobutyl groups (ligands) are grafted through flexible spacers made of polymeric chains obtained by polymerization of a monomer having the following formula: $CH_2{=}CH{-}CO{-}NH{-}C(CH_3)_2{-}CH_2{-}SO_3^-$ Gels of which ligands are grafted to the matrix through spacers have a "tentacle" structure that may facilitate the binding of the protein onto the ligand.

Various parameters were evaluated for the chromatography on Sartobind® S membrane (Sartorius) (support volume: 7 ml): the pH of the clarified harvest injected, which was in a range of from 7.5 to 8.0, the conductivity of the clarified harvest injected, which was in a range of from 4.5 mS/cm to 18 mS/cm, and the viral load injected, which was in a range of from 4 IU/ml to 11 IU/ml of support. Whatever the parameters studied the virus yields obtained were always ≤35%.

In the case of the chromatography on Mustang™ membrane S (Pall) (support volume: 10 ml), the pH and the conductivity of the clarified harvest were, respectively, 7.5 and 14 mS/cm, while the viral load injected was 32 IU/ml of support. The virus yield obtained was very low (≤10%).

The protocol that was used for the chromatography on Fractogel® EMD $SO_3^-$ as described in paragraph 1.3 was applied for the other gel chromatography supports. The only distinction is about the regeneration of the Toyopearl® SP 650 gel that was made in Tris 20 mM buffer containing NaCl 2M, pH=7.5. The same pH and conductivity conditions as those of the chromatography on Fractogel® EMD $SO_3^-$ were used. Except for the chromatography carried out on a Fractogel® EMD $SO_3^-$ support where the amount of virus found in the filtrate was about 5% of the total amount of virus injected in the chromatography column, the amounts of virus found in the filtrates of the other chromatography carried out on the other 3 supports (Capto™ S, SP Sepharose XL and Toyopearl® SP 650) were between 80 and 99% of the total amount injected. Accordingly, the harvested virus yields were very low (<10%).

Therefore, the structure of the ligands as well as the matrix play an important role since among all the strong cation exchanger chromatographic supports tested only the chromatographic support with sulfoisobutyl ligands grafted onto a polymethacrylate matrix gave good results.

In conclusion, out of all the anionic and cationic chromatographic supports tested, only a tentacle support comprising a polymethacrylate matrix onto which sulfoisobutyl groups are grafted like the support sold by Merck under the commercial name Fractogel®EMD $SO_3^-$ exhibits performance levels that are really exploitable from an industrial point of view, since the virus yield is >70% and removes more than 95% of the DNA in a single step.

EXAMPLE 2

Advantage of the Combination of a Step of Chromatography on Fractogel® EMD $SO_3^-$ Support with a Benzonase Treatment Step in the Method for Purifying the Rabies Virus In order to evaluate the advantage of this combination, this method was compared with a method for purifying the rabies virus by double benzonase treatment. Benzonase treatment is conventionally used to remove nucleic acids that are contained in a biological product. When this enzymatic treatment is repeated, the removal of the DNA is further increased.

A method for purifying the rabies virus which uses a "double benzonase treatment" was compared with the protocol of the invention, according to which a step of cation exchange chromatography on Fractogel® EMD $SO_3^-$ support was combined with a benzonase treatment.

In the case of the double benzonase treatment (UF-Bz-UF-Bz), the purification protocol that was used corresponds to that which is described in Table III below:

TABLE III

Purification of the rabies virus by double benzonase treatment (UF-Bz-UF-Bz).

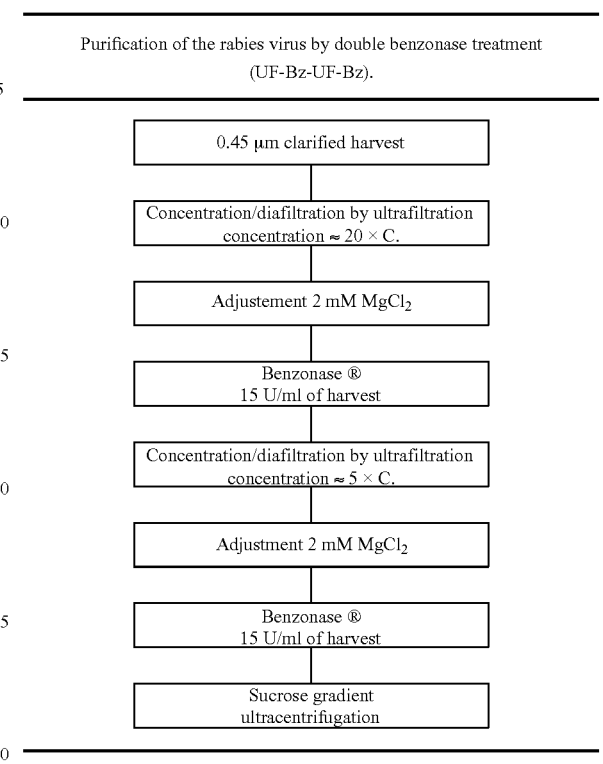

In the case of the treatment combining cation exchange chromatography on Fractogel® EMD $SO_3^-$ support and a benzonase treatment (CEX-UF-Bz), the purification method that was used corresponds to that which is described in Table IV below:

TABLE IV

Purification of the rabies virus by combination of cation exchange chromatography on Fractogel ® EMD $SO_3^-$ support and benzonase treatment (CEX-UF-Bz).

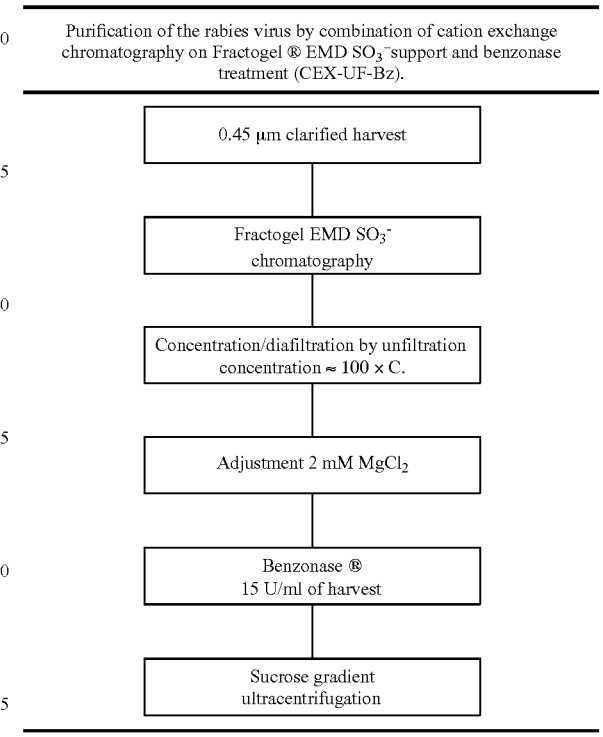

In both cases, the purification method was carried out starting from the same clarified harvest H1 having a volume of approximately 20 liters which was divided up into two equal parts.

In the case of the UF-Bz-UF-Bz method, the two concentrations were carried out on PES Medium Screen 1001(D membrane (PALL) combined with a diafiltration into 20 mM Tris buffer containing 150 mM NaCl, pH=7.5 by ultrafiltration, the first ultrafiltration step resulting in reduction of the clarified harvest volume by a factor of approximately 20, while the second ultrafiltration led to reduction of the clarified harvest volume by an overall factor of approximately 100. Before each benzonase treatment, a solution of $MgCl_2$ was added such that the concentration in the retentate was 2 mM. The benzonase treatment was carried out by adding 15 U/ml of crude harvest to the reaction medium and leaving the reaction medium for 2 hours at laboratory temperature.

In the case of the CEX-UF-Bz method, the chromatography step was carried out according to the methods described in paragraph 1-3. The eluate containing the purified virus was subsequently concentrated by a factor of approximately 5 and diafiltered and then benzonase-treated using the same protocol as that which was used in the UF-Bz-UF-Bz method.

In both methods, the ultracentrifugation step was carried out on 34-60% sucrose cushions with a 45 Ti type rotor at 21000 rpm for 2 h at +5° C. The fractions of the gradient containing the purified virus were recovered, combined, and then analyzed in terms of their DNA, virus and total protein content.

Table V below indicates, at the various stages of purification, the DNA, gpG and total-protein titers obtained as a function of the method used.

TABLE V

Assessment of the two purification methods

| Purification stage | Parameters | UF-Bz-UF-Bz method | CEX-UF-Bz method |
|---|---|---|---|
| Clarified harvest | volume | 9620 ml | 9620 ml |
| | DNA titer (ng/ml) | 270 | |
| | gpG titer (IU/ml) | 1.7 | |
| | DNA/gpG | $713 \times 10^3$ pg/4.5 IU | |
| UF-Bz-UF | volume | 100 ml | |
| | DNA titer (pg/ml) | NT | |
| | gpG titer (IU/ml) | 106.6 IU/ml | |
| CEX-UF | volume | | 100 ml |
| | DNA titer (pg/ml) | | NT |
| | gpG titer (IU/ml) | | 113 IU/ml |
| After UC | volume | 800 ml | 800 ml |
| | DNA titer (pg/ml) | $1.1 \times 10^3$ | <0.1 |
| | gpG titer (IU/ml) | 9.7 | 8.46 |
| | Total proteins/gpG | 36 µg/4.5 IU | 24 µg/4.5 IU |
| | DNA/gpG titer | 510 pg/4.5 IU | <50 pg/4.5 IU |
| | $Log_{10}$ reduction total DNA | 3.47 | >4.5 |
| | Virus yield* | 63% | 55% |

UF/Bz/UF: corresponds to the stage after the second ultrafiltration step but just before the second benzonase treatment in the UF-Bz-UF-Bz protocol.
CEX/UF: corresponds to the stage after the first ultafiltration step but just before the benzonase treatment in the CEX-UF-Bz protocol
After UC: corresponds to the stage where the fractions of the gradient containing the purified virus have been combined after ultracentrifugation and after the total volume has been adjusted such as that it is 12.5 times more concentrated than the volume of the clarified harvest.
*the virus yield is calculated on the basis of the gpG ELISA titers.

The results in table V show that the combination of chromatography on Fractogel® EMD $SO_3^-$ support followed by benzonase treatment (CEX-UF-Bz method) is much more effective in removing the DNA than a double benzonase treatment (UF-Bz-UF-Bz method). It is possible to reduce the amount of residual DNA by least a further 1 $Log_{10}$ using the CEX-UF-Bz method. These results were also confirmed on different volume scales.

It is also noted that the CEX-UF-Bz method also removes the contaminated proteins more effectively than the UF-Bz-UF-Bz method, since there was almost half the total proteins per unit of virus (expressed in the form of IU of gpG) (5.4 µg in the CEX-UF-Bz method instead of 8 µg per IU of gpG in the UF-Bz-UF-Bz method. This results from the fact that more than 65% of the proteins are removed during the chromatography step on Fractogel® EMD $SO_3^-$ support. These results show that the combination of a chromatography step on Fractogel® EMD $SO_3^-$ support with a benzonase treatment step in the method for purifying the rabies virus exerts a combined action on the removal of DNA in the clarified rabies virus harvests which is much greater than the effect observed during a double benzonase treatment.

What is claimed is:

1. A method of purifying rabies virus, the method comprising a single ion exchange chromatography purification wherein said ion exchange chromatography purification is a cation exchange chromatography purification comprising a) applying a supernatant of a culture of cells infected with the rabies virus to a cation exchange chromatography support under conditions in which the rabies virus binds to the support, wherein the support comprises a polymethacrylate matrix onto which sulfoisobutyl groups have been grafted by covalent bonding, and b) eluting the virus from the support.

2. The method as claimed in claim 1, wherein the culture supernatant of cells infected with the rabies virus is free of animal serum or free of any serum protein.

3. The method as claimed in claim 2, wherein the culture supernatant of cells infected with the rabies virus is free of any exogenous protein of animal origin.

4. The method as claimed in claim 3, wherein the culture supernatant of the cells infected with the rabies virus contains exogenous proteins of non-animal origin at a concentration <15 mg/l.

5. The method as claimed in claim 1, wherein the culture supernatant of cells infected with the rabies virus is free of any exogenous product of animal origin.

6. The method as claimed in claim 1, wherein the culture supernatant of cells infected with the rabies virus is a clarified supernatant.

7. The method as claimed in claim 1, wherein the amount of virus measured in the eluate corresponds to at least 70% of the amount of virus measured in the supernatant that was applied to the chromatographic support.

8. The method as claimed in claim 7, wherein the amount of total proteins measured in the eluate corresponds to less than 40% of the amount of total proteins measured in the supernatant that was applied to the chromatographic support and the amount of DNA measured in the eluate corresponds to less than 5% of the amount of DNA measured in the supernatant that was applied to the chromatographic support.

9. The method as claimed in claim 7, wherein the amount of total proteins measured in the eluate corresponds to less than 40% of the amount of total proteins measured in the supernatant that was applied to the chromatographic support and the amount of DNA measured in the eluate corresponds to less than 1% of the amount of DNA measured in the supernatant that was applied to the chromatographic support.

10. The method as claimed in claim 1, wherein, further comprising treating the eluate, optionally concentrated, with a nuclease.

11. The method as claimed in claim 10, wherein the nuclease is an endonuclease.

12. The method as claimed in claim 10, wherein the treated eluate is subjected to ultracentrifugation on a sucrose gradient and recovering the fraction(s) of the gradient that contain(s) the purified virus.

13. The method as claimed in claim 12, further comprising inactivating the purified rabies virus with a viral inactivation agent.

14. The method as claimed in claim 13, wherein the viral inactivation agent is β-propiolactone.

15. The method as claimed in claim 13, wherein the purification is conducted with products of non-animal origin only.

16. A method of manufacturing a rabies vaccine, the method comprising:
   a) infecting a culture of cells with the rabies virus,
   b) purifying the rabies virus from an infected-cell culture supernatant according to the method as claimed in claim 13,
   c) mixing the suspension obtained in b) with a storage buffer, and
   d) dividing the mixture obtained in c) into a single-dose or multidose vaccine(s).

17. A method for the manufacture of a rabies vaccine, the method comprising:
   a) infecting a culture of cells with the rabies virus,
   b) purifying the rabies virus from an infected-cell culture supernatant according to the method as claimed in claim 13,
   c) mixing the suspension of purified virus obtained in b) with a lyophilization buffer,
   d) dividing the mixture obtained in c) into a single-dose or multidose vaccine(s), and
   e) lyophilizing the vaccine dose(s).

* * * * *